(12) United States Patent
Ito et al.

(10) Patent No.: US 8,542,354 B2
(45) Date of Patent: Sep. 24, 2013

(54) INSPECTION APPARATUS

(75) Inventors: Masaaki Ito, Hitachinaka (JP); Minori Noguchi, Hitachinaka (JP); Shigeru Matsui, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 800 days.

(21) Appl. No.: 12/361,954

(22) Filed: Jan. 29, 2009

(65) Prior Publication Data

US 2009/0202138 A1 Aug. 13, 2009

(30) Foreign Application Priority Data

Jan. 31, 2008 (JP) ................................. 2008-020042

(51) Int. Cl.
*G01N 21/00* (2006.01)
(52) U.S. Cl.
USPC ........................................ 356/237.2; 382/149
(58) Field of Classification Search
USPC ............ 382/141, 145, 149; 356/237.2–237.5
See application file for complete search history.

(56) References Cited

U.S. PATENT DOCUMENTS

| | | | | |
|---|---|---|---|---|
| 6,885,460 B2 * | 4/2005 | Morita | ........................... | 356/514 |
| 7,292,393 B2 * | 11/2007 | Kvamme | ...................... | 359/566 |
| 7,489,393 B2 | 2/2009 | Biellak et al. | | |
| 2005/0253066 A1 * | 11/2005 | Watanabe et al. | ............. | 250/310 |
| 2006/0219930 A1 | 10/2006 | Lange | | |
| 2006/0256327 A1 * | 11/2006 | Vaez-Iravani et al. | ..... | 356/237.2 |
| 2007/0121104 A1 * | 5/2007 | Hendrix et al. | ............ | 356/237.2 |

FOREIGN PATENT DOCUMENTS

| | | |
|---|---|---|
| JP | 2004-271552 A | 9/2004 |
| JP | 2005-517906 | 6/2005 |
| JP | 2008-534963 | 8/2008 |
| WO | WO-2006/094115 A2 | 9/2006 |

OTHER PUBLICATIONS

Japanese Office Action, and English translation thereof, issued in Japanese Patent Application No. 2009-014878 dated Jun. 26, 2012.

* cited by examiner

*Primary Examiner* — Tarifur Chowdhury
*Assistant Examiner* — Jonathan Hansen
(74) *Attorney, Agent, or Firm* — McDermott Will & Emery LLP

(57) ABSTRACT

The present invention provides an inspection apparatus having a high throughput and high sensitivity with respect to a number of various manufacturing processes and defects of interest in inspection of a specimen such as a semiconductor wafer on which a pattern is formed. The apparatus illuminates with light the specimen having the pattern formed thereon, forms an image of the specimen on an image sensor through a reflective optics, and determines the existence/nonexistence of a defect. The reflective optics has a conjugate pair of Fourier transform optics. An aberration of the reflective optics is corrected off-axis. The reflective optics has a field of view in non-straight-line slit form on the specimen surface. Also, the optics is of a reflection type, includes a conjugate pair of Fourier transform optics and has a field of view in non-straight-line slit form. An optimum wavelength band is selected according to the specimen (FIG. 1).

32 Claims, 6 Drawing Sheets

(a)

(b)

INSPECTION APPARATUS

BACKGROUND OF THE INVENTION

1. Field of the Invention

The present invention relates to an inspection apparatus for inspecting a specimen on which a pattern is formed, e.g., a wafer in manufacture of a semiconductor device and, more particularly, to an optics in an optical inspection apparatus.

2. Background Art

Manufacture of a semiconductor device is divided into a front end process and a back end process. The front end process includes isolation forming, well forming, gate forming, source/drain forming, interlayer dielectric film forming and planarization. In the back end process, contact plug forming, interlayer dielectric film forming, planarization and metal wiring forming are repeated and passivation film forming is finally performed. In the course of the above-described manufacturing process, wafers are extracted and inspection of defects is performed. The defects include foreign particles on the wafer surface, scratches in the wafer surface, and pattern defects (such as shorts, opens and via missing). The first objective of defect inspection is to control the condition of the manufacturing apparatus, and the second objective of defect inspection is to ascertain a process step in which a defect is caused and the cause of the defect. With the miniaturization of semiconductor devices, a demand has arisen for increasing the sensitivity of inspection apparatuses.

For example, several hundreds of semiconductor devices (called chips) having patterns identical to each other are made on one wafer. With an inspection apparatus, therefore, a method of comparing images between chips adjacent or close to each other is mainly used.

An inspection apparatus in which a wafer is irradiated with light and dark-field images are compared is being widely used for inline inspection because of its high throughput. A first related known art is use of a refractive optics constituted of lenses with respect to a dark-field inspection apparatus in an ultraviolet region. For example, JP Patent Publication (Kohyo) No. 2005-517906 (patent document 1) relates to this art. The patent document 1 describes that the field of view of the optics is in the form of a straight slit having a longer-side size of several millimeters, and that high-throughput inspection can be performed by scanning a wafer along the shorter-side direction.

A second related known art is use of a reflective optics constituted of mirrors with respect to an inspection apparatus of a wide wavelength band from a visible light region to a vacuum ultraviolet region. In the second related art, the reflective optics can be used in a wide wavelength band because it has no chromatic aberration. Inspection with high sensitivity is made possible by selecting a wavelength band according to the manufacturing process and a defect of interest. For example, JP Patent Publication (Kohyo) No. 2008-534963 (patent document 2) relates to this art.

Patent document 1: JP Patent Publication (Kohyo) No. 2005-517906

Patent document 2: JP Patent Publication (Kohyo) No. 2008-534963

SUMMARY OF THE INVENTION

With the miniaturization of semiconductor devices, a demand has arisen for improving the sensitivity of an inspection apparatus while maintaining or improving the throughput. Solving this problem requires simultaneously satisfying two conditions with respect to a number of various manufacturing processes and defects of interest. The first condition is that the field of view of the optics (longer-side size in particular) is sufficiently large. The second condition is that an optimum wavelength band is selected according to the manufacturing process and a defect of interest.

The first related art can be applied to a deep ultraviolet region while satisfying the first condition. However, the first related art has a problem of being difficult to use in a wide wavelength band because the refractive optics has a chromatic aberration. There is also a problem that the absorption by lenses in the vacuum ultraviolet region is large, and therefore, it is presently impossible to use the refractive optics.

The second related art satisfies the second condition but has a problem in improving the throughput.

An object of the present invention is to provide an inspection apparatus having high throughput and high sensitivity with respect to a number of various manufacturing processes and defects of interest.

One feature of the present invention resides in that in an inspection apparatus which illuminates with light a specimen on which a pattern is formed, forms an image of the specimen on an image sensor through a reflective optics and determines the existence/nonexistence of a defect, the reflective optics has a conjugate pair of Fourier transform optics; an aberration of the reflective optics is corrected off-axis; and the reflective optics has a field of view in non-straight-line slit form on the specimen surface.

Another feature of the present invention resides in including a spatial filter on a Fourier transform plane of the Fourier transform optics.

Still another feature of the present invention resides in that diffracted light from the pattern of the specimen is blocked by the spatial filter.

A further feature of the present invention resides in that part of scattered light from the specimen is blocked by the spatial filter.

Still a further feature of the present invention resides in including a polarization filter on a Fourier transform plane of the Fourier transform optics.

Still a further feature of the present invention resides in that the field of view on the specimen surface is in circular-arc slit form.

Still a further feature of the present invention resides in that the optical axis of the reflective optics is inclined with respect to the direction of a normal to the specimen surface, and the field of view on the specimen surface is in slit form corresponding to a portion of an ellipse.

Still a further feature of the present invention resides in including a stage for scanning the specimen along a shorter-side direction of the field of view in slit form of the reflective optics.

Still a further feature of the present invention resides in that an error in scanning of the stage is measured and misalignment of an image of the specimen is corrected.

The present invention resides in that light in a predetermined single wavelength band is selected in a range from a visible light region to a vacuum ultraviolet region according to the specimen to illuminate the specimen.

Still a further feature of the present invention resides in that light in a plurality of predetermined wavelength bands are selected in a range from a visible light region to a vacuum ultraviolet region according to the specimen to illuminate the specimen.

Still a further feature of the present invention resides in that light in the plurality of wavelength bands is imaged on the single image sensor.

Still a further feature of the present invention resides in that light in the plurality of wavelength bands is imaged on a plurality of the image sensors.

Still a further feature of the present invention resides in that light in the predetermined wavelength band is selected from a single light source to illuminate the specimen.

Still a further feature of the present invention resides in that light in the predetermined wavelength band is selected from a plurality of light sources to illuminate the specimen.

Still a further feature of the present invention resides in that the specimen is illuminated with light in an extreme ultraviolet region.

Still a further feature of the present invention resides in that a layer region below the pattern of the specimen is substantially opaque to light with which the specimen is illuminated.

Still a further feature of the present invention resides in that an image of an inspection region and an image of a region adjacent or close to the inspection region are compared with each other to determine the existence/nonexistence of a defect.

Still a further feature of the present invention resides in that an image of an inspection region and an image obtained by simulation from data on the configuration of the pattern of the specimen are compared with each other to determine the existence/nonexistence of a defect.

Still a further feature of the present invention resides in that the image sensor is a time-delay-integration-type image sensor.

Still a further feature of the present invention resides in that an output array from the time-delay-integration-type image sensor and positions in the field of view of the reflective optics are associated with each other.

According to one aspect of the present invention, a sufficiently large longer-side size is secured in a field of view in non-straight-line slit form by using a reflective optics aberration-corrected in a wide wavelength band, and optimum wavelength bands are selected according to a number of various manufacturing processes and defects, thus enabling high-throughput and high-sensitivity inspection. According to another aspect of the present invention, the number of optical elements can be reduced and the effect of simplifying the optics can be obtained.

The above-described and other features of the present invention will be described in the following description.

DESCRIPTION OF SYMBOLS

Figure 1:
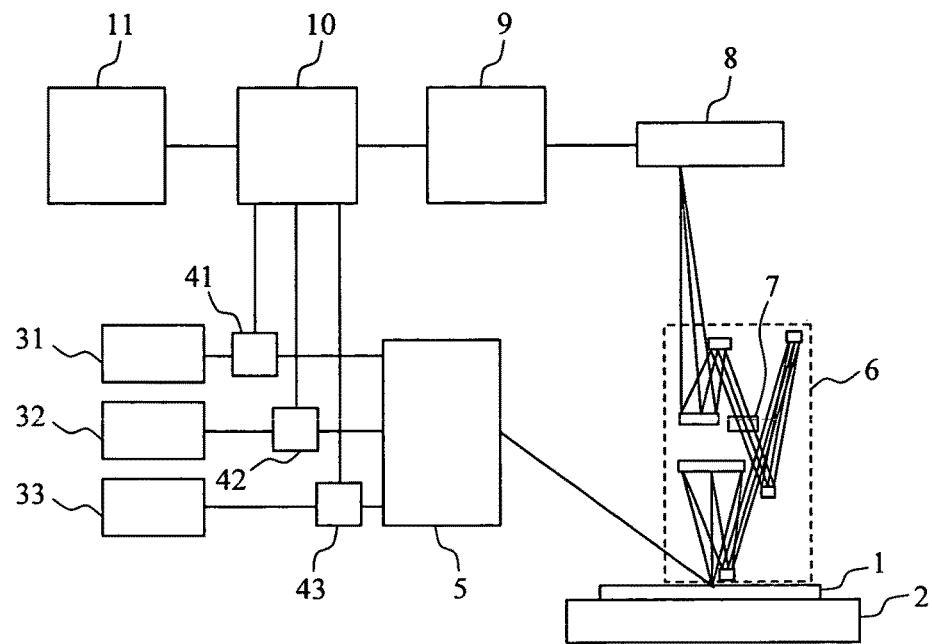
FIG. 1 is a diagram showing an embodiment of an inspection apparatus according to the present invention.

1 Wafer
2 Stage
31 Visible light laser
32 Ultraviolet laser
33 Deep ultraviolet laser
41, 42, 43 Attenuator
5 Illumination optics
6 Reflective optics
7 Spatial filter
8, 81, 82 Image sensor
9, 91, 92 Image processing system
10 Control system
11 Input-output operation system
12 Optical axis of reflective optics
13 Field of view of reflective optics on wafer
14 Field of view of reflective optics on TDI sensor
15 Output array from TDI sensor
16 Diffractive-optical element
17 Lamp
18 Wavelength filter
19 Vacuum ultraviolet light source
20 Vacuum chamber
21 Vacuum pump

DETAILED DESCRIPTION OF THE PREFERRED EMBODIMENTS

Herein after, embodiments of the present invention will be described with reference to the drawings.

Embodiment 1

A dark-field inspection apparatus for inspecting a semiconductor wafer will be described as an embodiment of the present invention. FIG. 1 schematically shows the construction of the inspection apparatus. Main components of the apparatus are a stage 2 on which a wafer 1 is mounted, a visible light laser 31, an ultraviolet laser 32, a deep ultraviolet laser 33, attenuators 41, 42, and 43, an illumination optics 5, a reflective optics 6, a spatial filter 7, an image sensor 8, an image processing system 9, a control system 10, and an input-output operation system 11.

When the wafer 1 is loaded in the inspection apparatus, an operator inputs information on the manufacturing process and a defect of interest to the input-output operation system 11. The control system 10 selects an optimum wavelength band such as described below by using this information and referring to a database accumulated in advance through a simulation or an experiment. The lasers 31, 32, and 33 emit light at all times to obtain outputs with stability. Light in a selected wavelength band is passed by adjusting the attenuators 41, 42, and 43 to illuminate a predetermined region on the wafer at oblique incidence through the illumination optics 5.

The reflective optics 6 is formed of six mirrors and is constructed so as to be rotationally symmetric about an optical axis (parallel to the direction of a normal to the wafer). Parameters of the optical design include the shapes of the mirrors and the distances between the surfaces of the mirrors. An aberration is corrected at a position at a predetermined distance from the optical axis. It is desirable to have, for example, aspherical mirrors in correcting an aberration in the reflective optics 6.

Since the optics is rotationally symmetric, a region where an aberration is corrected is in circular-arc form. The reflective optics has no chromatic aberration in theory and therefore has good imaging performance maintained in a wide wavelength band from a visible light region to a vacuum ultraviolet region.

Through the illumination optics 5, the field of view in the above-mentioned circular-arc slit form is illuminated with light at oblique incidence. Specularly reflected light from the wafer 1 travels out of the aperture of the reflective optics. As a result, a dark-field image is obtained. The size of the field of view in the longer-side direction is 5 mm or more. In ordinary cases, realizing the same field size with a refractive optics requires twenty or more lenses. The reflective optics 6 in the present embodiment is of a simple construction in which the number of mirrors is six.

The above-described reflective optics 6 is constituted by a conjugate pair of Fourier transform optics. The spatial filter 7 is disposed on a Fourier transform plane. Light transmitted through the spatial filter 7 is imaged on the image sensor 8.

The image sensor 8 is of a time delay integration (TDI) type. The charge transfer direction and the direction of scanning on the stage 2 coincide with the shorter-side direction of the field of view in slit form. An inspection image is obtained by matching the charge transfer rate and the stage scanning speed to each other. The inspection image is converted into a digital signal by an A/D converter (not shown) and the digital signal is recorded by the image processing system 9. The image processing system 9 has a recording of a reference image obtained from a chip adjacent or close to the inspected chip and having the same pattern as that of the inspected chip. Processing such as alignment is performed on the inspection image and the reference image, and a difference image between these images is thereafter output. The difference image is compared with a threshold value set in advance to determine the existence/nonexistence of a defect. The result of defect determination is transmitted to the control system 10 and is displayed on the input-output operation system 11 having a display after a predetermined inspection.

Figure 2:
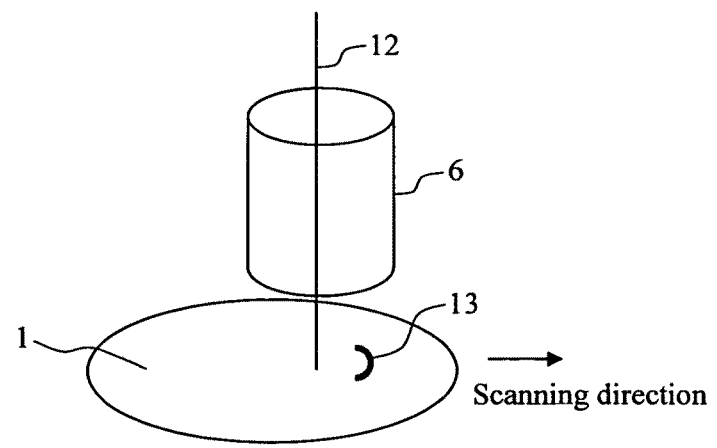
FIG. 2 is a diagram showing a field of view of a reflective optics on a wafer in the embodiment of the present invention.

FIG. 2 schematically shows a field of view 13 of the reflective optics on the wafer. The reflective optics 6 is placed above the wafer 1. The on-wafer field of view 13 of the reflective optics is positioned at a predetermined distance from an optical axis 12 of the reflective optics, and an aberration is corrected in the place. As described above, the longer-side size of the field of view is set sufficiently large and the wafer 1 is scanned along the shorter-side direction of the field of view (in the scanning direction of the arrow in FIG. 2), thereby achieving a high throughput. However, the stage on which the wafer is mounted is accompanied by scanning errors, such as variation in scanning speed, misalignment in the direction perpendicular to the scanning direction and yawing. Therefore, a stage scanning error is measured with a laser interferometer, misalignment of the inspection image is corrected, and the inspection image is thereafter compared with the adjacent image.

Description will next be made of the spatial filter. For example, the spatial filter is formed of cells two-dimensionally arrayed and is capable of setting a shielding portion in any form. Diffracted light from a pattern on the wafer becomes background noise and therefore reduces the signal-to-noise ratio in defect detection. There are many repetitive patterns in a semiconductor device. In such a case, diffracted light is in dot or straight line form in the Fourier transform plane.

Figure 3:
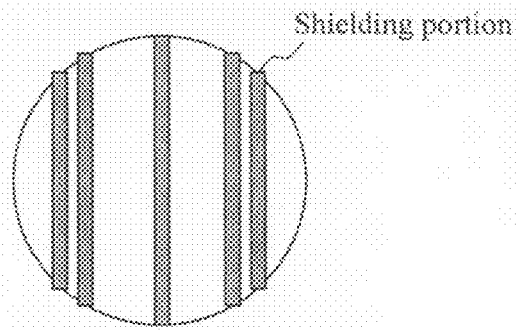
FIG. 3 is a diagram showing a spatial filter which blocks diffracted light from a repetitive pattern on the wafer in the embodiment of the present invention.

Then, it is possible to block diffracted light from a recursive pattern by setting a shielding portion in straight line form in the spatial filter as shown in FIG. 3. The signal-to-noise ratio can be improved in this way. Also, scattered light due to the surface roughness of the wafer or pattern edge roughness also becomes background noise to reduce the signal-to-noise ratio. It is known that such scattered light is strongly produced in a particular direction.

Figure 4:
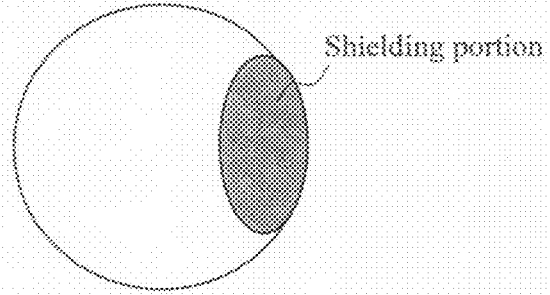
FIG. 4 is a diagram showing a spatial filter which blocks part of scattered light from the wafer in the embodiment of the present invention.

Then, it is possible to block unnecessary scattered light by setting a shielding portion in a particular portion of the spatial filter as shown in FIG. 4. The signal-to-noise ratio can be improved in this way.

In ordinary cases, scattered light due to a defect and scattered light due to the surface roughness of the wafer or pattern edge roughness differ in polarization state. In such a case, the signal-to-noise ratio of a defect can be improved by placing a polarization filter on the Fourier transform plane.

In the present embodiment, as described above, selection of a wavelength band is enabled according to a process and a defect of interest. Description will be made of details below.

In a case where foreign particles on an oxide film are inspected, thin-film interference occurs because the oxide film is transparent. As a result, because of film thickness nonuniformity of the oxide film, the scattered light intensity of defects and the scattered light intensity of a background pattern vary largely. In reducing the bad influence of such thin-film interference, illumination with light in a plurality of wavelength bands is highly effective. The control system therefore selects a combination of deep ultraviolet light and ultraviolet light, a combination of deep ultraviolet light and visible light or a combination of ultraviolet light and visible light by referring to the above-described database. Further, the control system selects an optimum value of the intensity ratios of the wavelength bands and automatically controls the transmissions through the attenuators.

In a case where foreign particles on a metal film are inspected, the intensity of scattered light from defects increases if the wavelength becomes shorter but the intensity of scattered light due to the surface roughness of the metal film and the intensity of scattered light due to the pattern edge roughness also increase. The control system therefore selects, by referring to the above-described database, such a wavelength band that the signal-to-noise ratio is maximized. In a case where the wafer under inspection is not included in the database, the operator may manually select a wavelength band to perform conditioning on a trial basis.

While a visible light laser, an ultraviolet laser and a deep ultraviolet laser are incorporated as light sources in the above-described embodiment, a sensitivity improvement effect can also be obtained with respect to a number of various manufacturing processes and defects of interest by incorporating a visible light laser and an ultraviolet laser, a visible light laser and a deep ultraviolet laser, or an ultraviolet laser and a deep ultraviolet laser.

Description will next be made of the sensor. While the field of view of the reflective optics is circular-arc slit form (two-dimensional), the output array from the TDI sensor is in line form (one-dimensional). The deference between them will not cause any problem for determination of the existence/nonexistence of a defect, but there is a need to associate the output array from the TDI sensor with positions in the field of view in order to ascertain the coordinate position of a defect.

Figure 5:
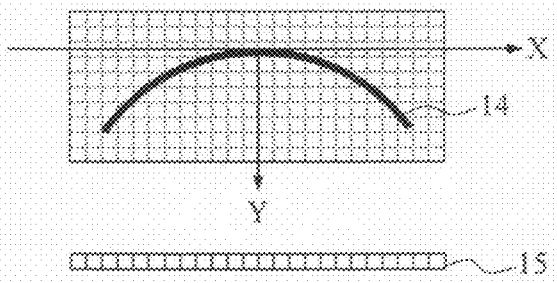
FIG. 5 is a diagram showing a field of view of the reflective optics on a TDI sensor in the embodiment of the present invention.

FIG. 5 shows the field of view on the TDI sensor. A X-direction represents the longer-side direction, and a Y-direction represents the shorter-side direction. Reference numeral 14 denotes the field of view on the TDI sensor in the reflective optics. Reference numeral 15 denotes the output array from the TDI sensor. Squares in FIG. 5 correspond to pixels of the TDI sensor. The longer-side direction of the TDI sensor is shown as a X-direction and the shorter-side direction is shown as a Y-direction, thus forming a coordinate system. If the radius of a circular arc on the TDI sensor is R, positions (X, Y) in the field of view can be associated by computation shown by expression (1).

$$Y = R(1 - \cos(\sin^{-1}(X/R))) \quad \text{(Expression 1)}$$

While the image sensor is a TDI sensor in the above-described embodiment, a two-dimensional sensor such as a CCD sensor may alternatively be used. A CCD sensor has a lower sensitivity but is lower in cost in comparison with a TDI sensor. Also, the need for the above-described computation for association is eliminated because the pixels of the CCD sensor correspond to positions in field of view of the reflective optics in one-to-one correspondence.

Embodiment 2

Figure 6:
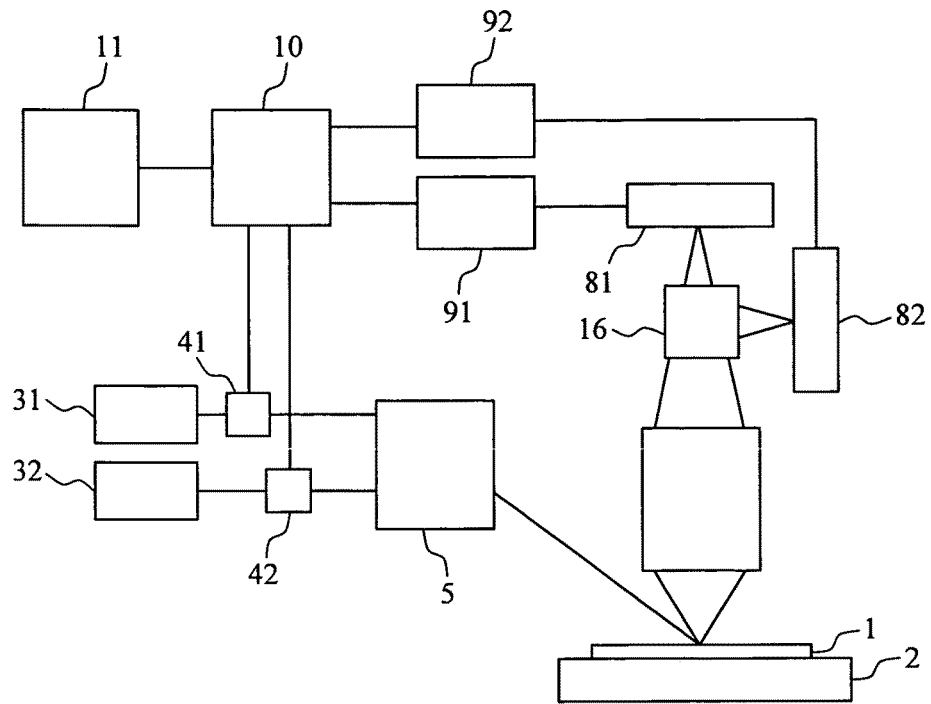
FIG. 6 is a diagram showing another embodiment of the inspection apparatus according to the present invention.

An embodiment of the present invention preferable in a case where a plurality of defects of interest exist on a wafer will be described with reference to FIG. 6. The same reference numerals as those in FIG. 1 denote identical or corresponding components. In this embodiment, diffractive-optical elements 16 are disposed on the exit side of the reflective optics 6 to separate light into wavelength bands. As each diffractive-optical element, a diffraction grating, a prism or the like can be used. Separated light is imaged on an image sensor 81 and an image sensor 82 in correspondence with the wavelength bands. An optimum wavelength band can be selected with respect to each detect of interest. Therefore, an image of a high signal-to-noise ratio can be obtained.

Embodiment 3

Figure 7:
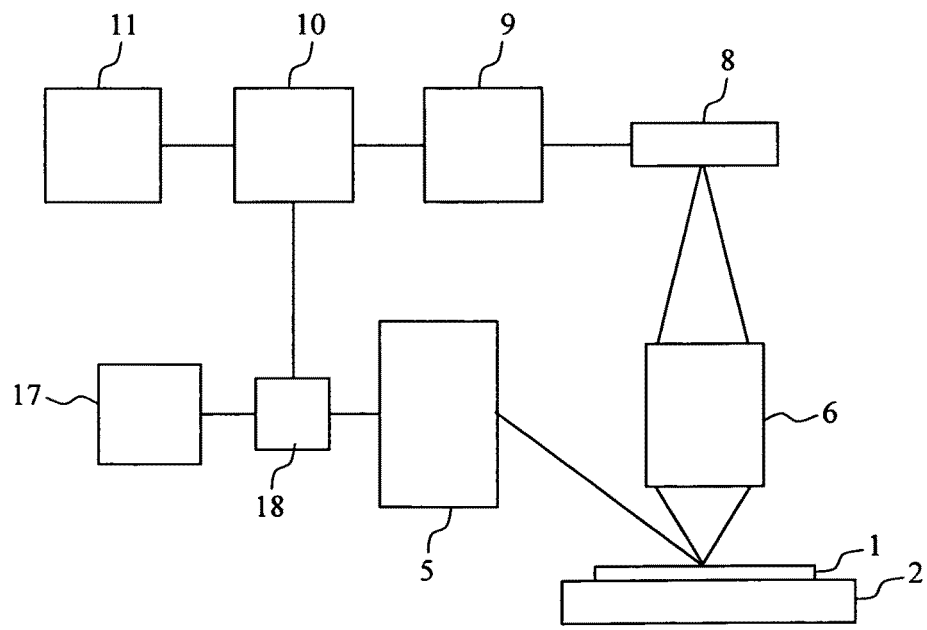
FIG. 7 is a diagram showing another embodiment of the inspection apparatus according to the present invention.

Another embodiment of the present invention will be described with reference to FIG. 7. The same reference numerals as those in FIG. 1 denote identical or corresponding components. In this embodiment, a lamp 17 which emits light in a wide wavelength band from a visible light region to a deep ultraviolet region is used as a light source, and a wavelength filter 18 allows light in a predetermined wavelength band to pass through. The lamp has a lower output per wavelength band in comparison with lasers but is capable of making finer selections from wavelength bands because it emits a continuous spectrum of light. Finer selections from wavelength bands can be made in the wavelength filter 18 on the basis of a command from the control system 10. The present embodiment is highly effective in reducing the bad influence of thin-film interference. Also, the construction of the apparatus is simplified in comparison with a case where a plurality of lasers are incorporated.

Embodiment 4

Figure 8:
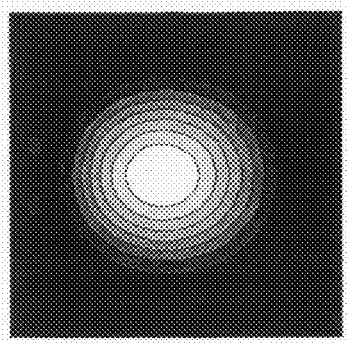
FIG. 8 is a diagram showing a distribution of the intensity of scattered light from a defect.
Figure 8:
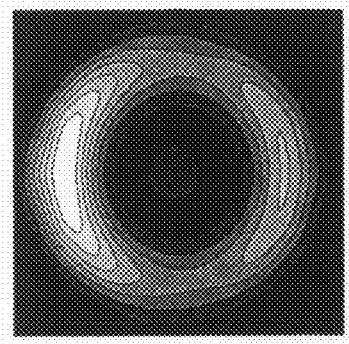

A distribution of the intensity of scattered light from defects on an oxide film varies largely depending on the oxide film thickness. FIG. 8 shows a gray-scale display of a distribution of the intensity of scattered light on an observation plane perpendicular to a normal to a wafer surface. There are a case where strong scattering in the direction of a normal to the wafer occurs as shown in (a), and a case where strong oblique scattering occurs as shown in (b).

Figure 9:
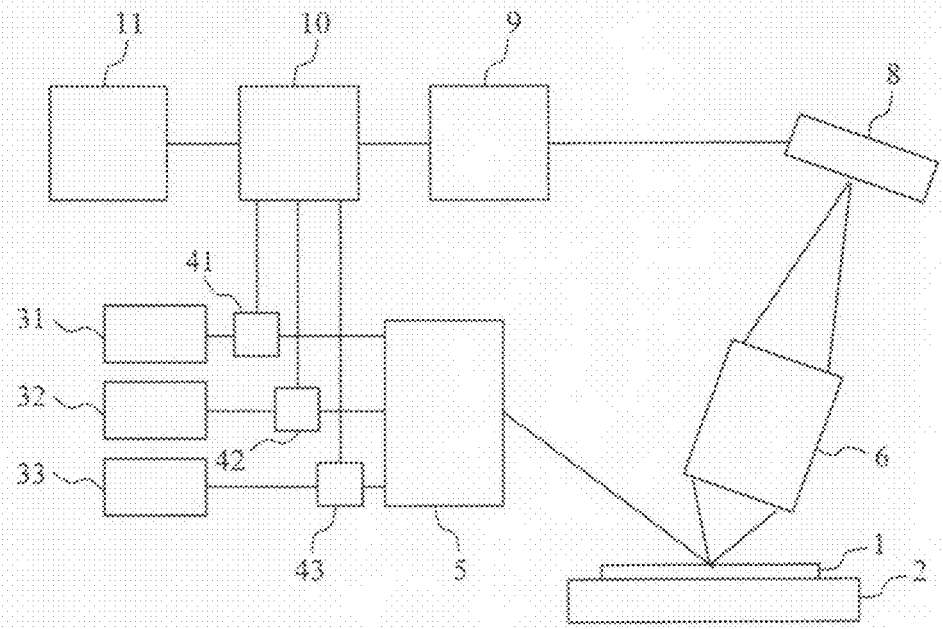
FIG. 9 is a diagram showing another embodiment of the inspection apparatus according to the present invention.

An embodiment of the present invention preferable in a case where strong oblique scattering of light occurs due to a defect will be described with reference to FIG. 9. The same reference numerals as those in FIG. 1 denote identical or corresponding components. In this embodiment, the optical axis of the reflective optics 6 is inclined with respect to the direction of a normal to the wafer surface to capture obliquely scattered light. Since an aberration of the reflective optics 6 is corrected in a circular-arc region in a plane perpendicular to the optical axis, the aberration-corrected region on the wafer in the present embodiment is elliptical. Therefore, illumination light is provided in a field of view in slit form corresponding to a portion of the ellipse by the illumination optics 5. It is desirable to use, for example, aspherical mirrors for correction of an aberration in the reflective optics 6.

Embodiment 5

Figure 10:
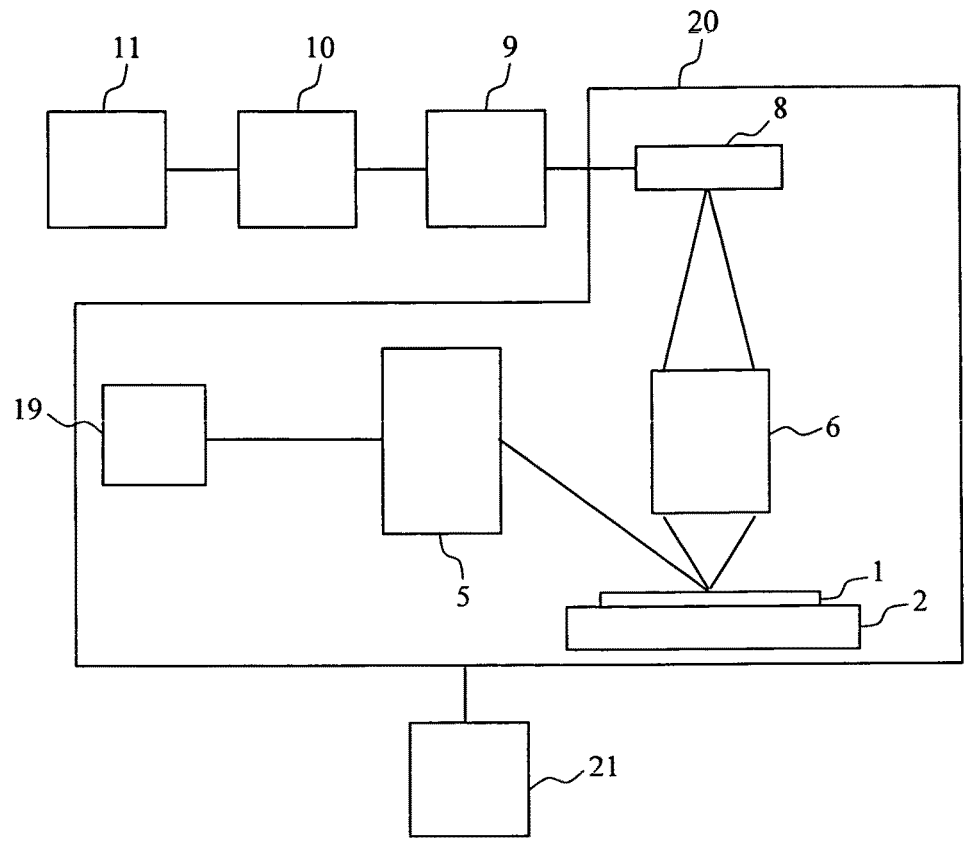
FIG. 10 is a diagram showing another embodiment of the inspection apparatus according to the present invention.

An inspection apparatus using vacuum ultraviolet light will be described as another embodiment of the present invention with reference to FIG. 10. The same reference numerals as those in FIG. 1 denote identical or corresponding components. In a vacuum chamber 20 in which an evacuated state is realized with a vacuum pump 21, the stage 2 on which a wafer 1 is mounted, the illumination optics 5, the reflective optics 6 and the image sensor 8 are provided.

A vacuum ultraviolet laser is used as the vacuum ultraviolet light source 19. For example, an Ar laser having a wavelength of 126 nm is used. The optical path is placed inside the vacuum chamber 20 in order to avoid absorption of light by air. An F2 laser having a wavelength of 157 nm may alternatively be used. At a wavelength of 157 nm, there is no need for a vacuum; a nitrogen atmosphere may be used in order to avoid absorption of light by oxygen. As a coating material for mirrors in a vacuum ultraviolet region, a film of a metal such as Al or Au is used. Since the reflectance is high even at normal incidence (at an angle of incidence close to zero degree), sufficiently high power of light imaged on the sensor can be obtained.

Resist pattern inspection in a lithography process according to the above-described embodiment will be described. In a lithography process, a systematic defect generated in a particular place where a process margin is small (called a hot spot) has become a serious consideration as patterns are made finer. Hot spot defects include a short in a narrow gap and a small change in pattern size, and such defects have become difficult to detect with the conventional inspection apparatus using a deep ultraviolet light with a wavelength of 266 nm. Since the resolution of the optics is in inverse proportion to the wavelength, the defect sensitivity can be improved by using vacuum ultraviolet light. With vacuum ultraviolet light, an effect described below is further obtained.

Figure 11:
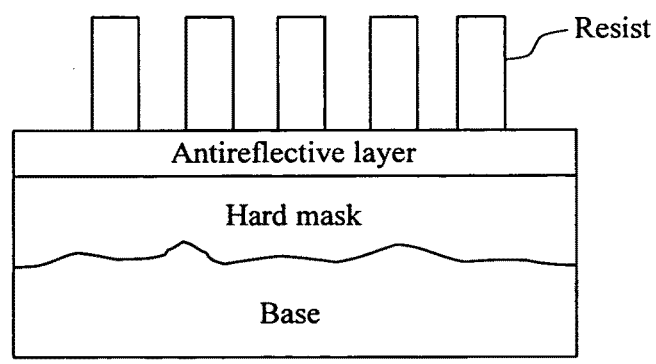
FIG. 11 is a diagram showing the structure of a wafer in section in resist pattern inspection in the embodiment of the present invention.

FIG. 11 shows the structure of a wafer in section in resist pattern inspection. In FIG. 11, a structure is shown which has a base layer formed as a base, a hard mask formed on the base layer, an antireflective layer formed on the hard mask and a resist pattern formed on the antireflective layer. An ordinary base has a large surface roughness and scattered light from such a base becomes background noise to impede defect detection. Because vacuum ultraviolet light is easily absorbed in an antireflective layer or a hard mask in comparison with deep ultraviolet light, scattered light from the base is largely reduced. Thus, in the inspection apparatus for inspecting a specimen, the layer region below the pattern of the specimen is substantially opaque to light with which the specimen is illuminated. As a result, the signal-to-noise ratio is improved and defect detection is made easier.

Embodiment 6

A systematic defect occurs at the same positions in a plurality of chips. It is, therefore, difficult to determine such a defect by comparison between the chips.

Figure 12:
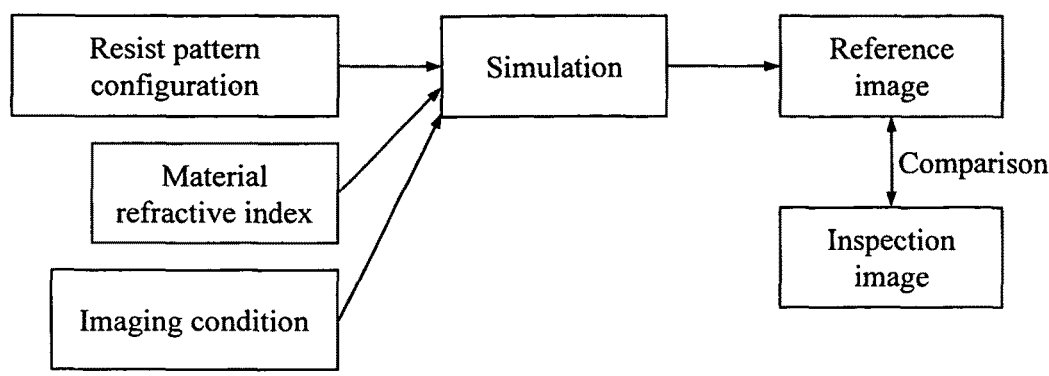
FIG. 12 is a diagram showing a method of determining a systematic defect in the embodiment of the present invention.

A defect determination method not based on chip comparison will be described with reference to FIG. 12. In ordinary cases, a resist pattern configuration in a hot spot is obtained by a lithography simulation in pattern designing. An image of the pattern free from any defect is obtained by simulation using data on the resist pattern configuration, data on refractive indices of materials including the resist material and data on imaging conditions which are optical conditions such as the wavelength and the angle of incidence of illumination light and the numerical aperture of the reflective optics. This simulation image is compared as a reference image with the inspection image, thus enabling determination of the existence/nonexistence of a systematic defect. The above-described defect determination method can be applied to optical inspection apparatuses in general without being limited to the reflective optics.

It is also possible to detect a defect in a mask for lithography by inspecting a resist pattern on a wafer. This is effective in monitoring adhesion of foreign particles on a mask in extreme ultraviolet lithography in particular, because a pellicle for protecting the mask cannot be used.

Embodiment 7

An inspection apparatus using extreme ultraviolet light with a wavelength shorter than that of vacuum ultraviolet light will be described as another embodiment of the present invention. For example, a laser-induced plasma source or a gas discharge plasma source can be used as an extreme ultraviolet light source. The optical path is placed inside the vacuum chamber in order to avoid absorption of light by air. In ordinary cases, in an extreme ultraviolet region, the normal-incidence reflectance of a metal film mirror is extremely low. At a wavelength of 13 nm, however, a high reflectance can be obtained by a multilayer mirror having an alternately stacked several ten layers of Mo and Si. Also, the amount of scattered light from a defect can be increased by increasing the angle of incidence of illumination light on a wafer. The resolution of the optics in an extreme ultraviolet region is higher than that in a vacuum ultraviolet region by an order of magnitude. Therefore, an extremely small defect can be detected.

The embodiments have been described with respect to a semiconductor wafer dark-field inspection apparatus. However, the present invention is not limited to the dark-field inspection apparatus. The present invention can also be applied to a bright-field inspection apparatus.

The reflective optics of the present invention may include an optical element such as a beam splitter as well as mirrors.

The inspection apparatus of the present invention is also applicable to inspection of specimens such as a semiconductor lithography mask and a liquid crystal device on which a pattern is formed.

As described above, an inspection apparatus having a high throughput and high sensitivity in inspection of a specimen such as a semiconductor wafer on which a pattern is formed can be provided if, for example, the optics is of type including a conjugate pair of Fourier transform optics; the field of view is in non-straight-line slit form; and an optimum wavelength band is selected according to the specimen.

What is claimed is:

1. An inspection apparatus which determines an existence and a non-existence of a defect, the apparatus comprising:
   an illumination system which illuminates a specimen with light; and
   a Fourier transform system comprising:
      a first Fourier transform unit which includes first reflective elements;
      a second Fourier transform unit which includes second reflective elements; and
      an image sensor which acquires an image by using reflected light from the second reflective elements, wherein:
   the first Fourier transform unit and the second Fourier transform unit are conjugate,
   the first Fourier transform unit includes an objective element which reflects light from the specimen,
   an aberration of the Fourier transform system is corrected off-axis, and
   a field of view of the Fourier transform system on a surface of the specimen is in non-straight-line slit form.

2. The inspection apparatus according to claim 1, further comprising a spatial filter on a Fourier transform plane between the first Fourier transform unit and the second Fourier transform unit.

3. The inspection apparatus according to claim 2, wherein diffracted light from the pattern of the specimen is blocked by the spatial filter.

4. The inspection apparatus according to claim 2, wherein part of scattered light from the specimen is blocked by the spatial filter.

5. The inspection apparatus according to claim 1, further comprising a polarization filter on a Fourier transform plane between the first Fourier transform unit and the second Fourier transform unit.

6. The inspection apparatus according to claim 1, wherein the field of view on the specimen surface is in circular-arc slit form.

7. The inspection apparatus according to claim 1, wherein the optical axis of the Fourier transform system is inclined with respect to the direction of a normal to the specimen surface, and the field of view on the specimen surface is in slit form corresponding to a portion of an ellipse.

8. The inspection apparatus according to claim 1, further comprising a stage for scanning the specimen along a shorter-side direction of the field of view in slit form on the specimen surface.

9. The inspection apparatus according to claim 8, further comprising a laser interferometer, wherein an error in scanning of the stage is measured by the laser interferometer and misalignment of an image of the specimen is corrected.

10. The inspection apparatus according to claim 1, wherein light in a predetermined single wavelength band is selected in a range from a visible light region to a vacuum ultraviolet region according to the specimen to illuminate the specimen.

11. The inspection apparatus according to claim 1, wherein light in a plurality of predetermined wavelength bands are selected in a range from a visible light region to a vacuum ultraviolet region according to the specimen to illuminate the specimen.

12. The inspection apparatus according to claim 11, wherein light in the plurality of wavelength bands is imaged on a single image sensor.

13. The inspection apparatus according to claim 11, wherein light in the plurality of wavelength bands is imaged on a plurality of the image sensors.

14. The inspection apparatus according to claim 10, wherein light in the predetermined wavelength band is selected from a single light source to illuminate the specimen.

15. The inspection apparatus according to claim 10, wherein light in the predetermined wavelength band is selected from a plurality of light sources to illuminate the specimen.

16. The inspection apparatus according to claim 1, wherein the specimen is illuminated with light in an extreme ultraviolet region.

17. The inspection apparatus according to claim 1, wherein a layer region below the pattern of the specimen is substantially opaque to light with which the specimen is illuminated.

18. The inspection apparatus according to claim 1, wherein an image of an inspection region and an image of a region adjacent or close to the inspection region are compared with each other to determine the existence/nonexistence of the defect.

19. The inspection apparatus according to claim 1, further comprising: an image processing system, wherein an image of an inspection region and an image obtained by simulation from data on the configuration of the pattern of the specimen are compared with each other to determine the existence/nonexistence of a defect by the image processing system.

20. The inspection apparatus according to claim 1, wherein the image sensor is a time-delay-integration-type image sensor.

21. The inspection apparatus according to claim 20, wherein an output array from the time-delay-integration-type image sensor and positions in the field of view of the reflective optics are associated with each other.

22. The inspection apparatus according to claim 1, further comprising an aspherical mirror with which an aberration of the Fourier transform system is corrected off-axis.

23. The inspection apparatus according to claim 11, wherein light in the predetermined wavelength bands is selected from a single light source to illuminate the specimen.

24. The inspection apparatus according to claim 12, wherein light in the predetermined wavelength bands is selected from a single light source to illuminate the specimen.

25. The inspection apparatus according to claim 13, wherein light in the predetermined wavelength bands is selected from a single light source to illuminate the specimen.

26. The inspection apparatus according to claim 11, wherein light in the predetermined wavelength bands is selected from a plurality of light sources to illuminate the specimen.

27. The inspection apparatus according to claim 12, wherein light in the predetermined wavelength bands is selected from a plurality of light sources to illuminate the specimen.

28. The inspection apparatus according to claim 13, wherein light in the predetermined wavelength bands is selected from a plurality of light sources to illuminate the specimen.

29. The inspection apparatus according to claim 1, wherein the illumination system is a multiple wavelength illumination system and changes wavelengths as function of a condition of the specimen.

30. The inspection apparatus according to claim 1, wherein said sensor includes:
   a plurality of pixels, and the pixels of the sensor correspond to positions in field of view of the Fourier transform system in one-to-one correspondence.

31. The inspection apparatus according to claim 1, further comprising:
   a diffraction element arranged at an output side of the Fourier transform system; and
   a plurality of sensors which detect a light diffracted by the diffraction element.

32. The inspection apparatus according to claim 1, wherein the Fourier transform system comprises a plurality of mirrors, and an arrangement of the mirrors is rotation symmetric relative to a normal of the specimen.

* * * * *